United States Patent
Dillon

(10) Patent No.: US 9,414,970 B2
(45) Date of Patent: Aug. 16, 2016

(54) WRINKLE REDUCING SKIN PATCH, PROCESS OF MANUFACTURE AND USEFUL ARTICLES THEREOF

(75) Inventor: Mark E. Dillon, Center Valley, PA (US)

(73) Assignee: BIO MED SCIENCES, INC., Allentown, PA (US)

( * ) Notice: Subject to any disclaimer, the term of this patent is extended or adjusted under 35 U.S.C. 154(b) by 1171 days.

(21) Appl. No.: 12/288,911

(22) Filed: Oct. 24, 2008

(65) Prior Publication Data

US 2009/0234382 A1    Sep. 17, 2009

Related U.S. Application Data

(60) Provisional application No. 61/000,201, filed on Oct. 24, 2007.

(51) Int. Cl.

| | |
|---|---|
| *A61F 5/08* | (2006.01) |
| *A61F 13/12* | (2006.01) |
| *A61K 8/02* | (2006.01) |
| *A61K 8/81* | (2006.01) |
| *A61K 8/891* | (2006.01) |
| *A61Q 19/02* | (2006.01) |
| *A61Q 19/08* | (2006.01) |
| *A61F 13/00* | (2006.01) |

(52) U.S. Cl.
CPC ............. *A61F 13/124* (2013.01); *A61F 13/122* (2013.01); *A61K 8/0208* (2013.01); *A61K 8/8123* (2013.01); *A61K 8/891* (2013.01); *A61Q 19/02* (2013.01); *A61Q 19/08* (2013.01); *A61F 2013/00374* (2013.01); *A61K 2800/594* (2013.01)

(58) Field of Classification Search
CPC ................ A61F 13/124; A61F 13/122; A61F 2013/00374; A61Q 19/08; A61Q 19/02; A61K 8/8123; A61K 8/0208; A61K 8/891; A61K 2800/594
USPC ..................................................... 606/204.35
See application file for complete search history.

(56) References Cited

U.S. PATENT DOCUMENTS

| | | | |
|---|---|---|---|
| 5,968,533 A | 10/1999 | Porter et al. | |
| 5,980,923 A * | 11/1999 | Dillon | ........................... 424/402 |

(Continued)

FOREIGN PATENT DOCUMENTS

WO    WO 2006059078 A1 *    6/2006 ............... A61K 8/02

*Primary Examiner* — Amy R Weisberg
(74) *Attorney, Agent, or Firm* — John F. A. Earley, III; Frank J. Bonini, Jr.; Harding, Earley, Folllmer & Frailey, P.C.

(57) ABSTRACT

This invention relates to a novel method of reducing the appearance of rhytides ("facial wrinkles") and/or infra-orbital shadows ("dark circles") under the eyes, and striae ("stretch marks"), or lentigo senilis ("age spots"), and hyper/hypo pigmentation on other anatomical areas. Particularly, this invention relates to a topical patch worn on the skin that in a preferred embodiment incorporates two distinct layers, each providing useful features and together providing a novel article and method of improving skin cosmesis. Ease of use, patient comfort and cost effectiveness are provided. The patch is applied to the affected area and preferably worn at least several hours and more preferably worn overnight. The product increases the hydration level of the skin over which it is applied. There is a slight increase to the volume of the local superficial tissue, which serves to tighten the overlying skin and reduce the size and quantity of fine wrinkles at least temporarily. Various active ingredients, such as peptides, vitamin compounds, antioxidants, growth factors, glycolic or alphahydroxy acids, etc., may be incorporated into the present invention thereby providing an enhanced effect or other perceived advantage in the market.

25 Claims, 1 Drawing Sheet

(56) References Cited

U.S. PATENT DOCUMENTS

| | | | |
|---|---|---|---|
| 6,346,255 B1* | 2/2002 | Fotinos | 424/401 |
| 6,937,893 B2 | 8/2005 | Danz et al. | |
| 7,087,135 B2* | 8/2006 | Dillon | 156/285 |
| 2002/0131948 A1* | 9/2002 | Toumi et al. | 424/70.12 |
| 2005/0191337 A1* | 9/2005 | Gueret | A61K 8/0208 424/448 |
| 2007/0110737 A1* | 5/2007 | Mishra | A61K 8/983 424/93.72 |
| 2008/0181953 A1* | 7/2008 | Cassin | 424/486 |
| 2008/0305132 A1* | 12/2008 | Karol | 424/401 |

* cited by examiner

WRINKLE REDUCING SKIN PATCH, PROCESS OF MANUFACTURE AND USEFUL ARTICLES THEREOF

BACKGROUND OF THE INVENTION

1. Field of the Invention

This invention relates to a novel method of reducing the appearance of rhytides ("facial wrinkles") and/or infra-orbital shadows ("dark circles") under the eyes, and striae ("stretch marks"), lentigo senilis ("age spots"), and hyper/hypo pigmentation on other anatomical areas. Particularly, this invention relates to a topical patch worn on the skin that in a preferred embodiment incorporates two distinct layers, each providing useful features and together providing a novel article and method for improving skin cosmesis. Ease of use, patient comfort and cost effectiveness are provided.

2. Description of the Prior Art

Wrinkles occur on the face as a result of several factors including the gradual loss of skin elasticity, the long-term effects of gravity, exposure to ultraviolet radiation from the sun as well as the natural process of losing fat tissue in certain areas of the face as one ages. Cosmetic makeup or surgical interventions are often used to reduce the appearance or presence of facial wrinkles. Depending on the severity of the condition and the patient's motivation for remedy, there exists a wide variety of treatment options. Protocols range from simple topical applications to invasive surgery.

The appearance of superficial fine lines can be easily reduced with ordinary cosmetic makeup available in a wide range of formats and presentations. Topical applications have also been used to reduce the appearance of fine wrinkles by delivering active ingredients such as antioxidants, vitamins and other agents to the skin. As one escalates up the severity/motivational scale, chemical peels using agents such as phynel, trichloroacetic acid or alphahydroxy acid become an option. These techniques do have a rejuvenating effect on the skin, but are painful and may cause a significant period of erythema and/or edema after the procedure. In addition, chemical peels can present a risk of scarring due to excessive depth of penetration.

Another method of reducing facial wrinkles is soft-tissue augmentation using a cannula to implant either natural tissue or a synthetic biomaterial under the skin. Volume is thus added to the underlying tissue thereby reducing sagging and wrinkles of the overlying skin. Autologous tissue, collagen from allogeneic or xenogeneic sources, expanded polytetrafluoroethylene and a broad range of other materials have been used for this purpose.

More drastic means of alleviating facial wrinkles include surgical rhytidectomy or "face-lift," where the patient's skin is lifted from the underlying tissue and retracted. The excess skin is then trimmed and the remaining skin is anchored in a tightened position using sutures.

Botulinum toxin is an additional technique that is commonly used for the reduction of facial wrinkles. Botox® (Allergan, Inc. Irvine, Calif.) is a purified protein produced by the clostridium botulinum bacterium. Botox reduces the activity of the muscles that cause wrinkles and "frown lines" when injected. While this procedure has become widely practiced it is nonetheless invasive, painful and requires periodic re-treatments. Because it essentially paralyses the underlying musculature, a "frozen expression" effect is sometimes experienced.

Frownies® (B&P Company Dayton, Ohio) are described by the marketer as "facial pads made from natural, skin-friendly materials. Frownies are applied to the forehead and corners of the eyes and mouth to gently re-educate the underlying muscles to assume their correct, relaxed and natural appearance. Frownies, in fact, allow the deep expression lines to heal leaving younger, relaxed-looking skin." The product is promoted as a "Botox Alternative." The Company claims "results were achieved after using Frownies every night for only 3 weeks."

In recent years laser resurfacing and rejuvenation techniques have emerged. Ablative techniques are used to remove the epidermis and a precisely controlled amount of the dermis, thereby removing sun damaged skin and providing a rejuvenating effect as the skin heals and the native collagen remodels. My U.S. Pat. No. 4,832,009, which is incorporated herein by reference, describes a dressing comprising a semi-interpenetrating polymer network of polytetrafluoroethylene and silicone, which is commonly used as a temporary skin replacement for such laser inflicted wounds. (Suarez, et. al., A novel dressing for skin resurfacing. Dermatol Surg 1998; 24:567-570)

My U.S. Pat. Nos. 5,656,279, 5,759,560, 5,980,923 and 7,087,135, all of which are incorporated herein by reference, describe silicone-based scar management products that are used for reducing and preventing scars subsequent to dermal injury and methods of their manufacture. These products are believed to work by hydration, wherein the silicone material provides moisturizing effect that reduces the tendency for scar formation or reduces an existing scar by accelerating the collagen remodeling process. (Chang, C C, et. al., Hydration, not silicone, modulates the effects of keratinocytes on fibroblasts. J Surg Res 1995; 59:705-11)

SUMMARY OF THE INVENTION

I have unexpectedly discovered that silicone-containing material, such as the scar management material of my patents cited above may be used to reduce the appearance of facial wrinkles, at least temporarily. The silicone-containing material is applied to the affected area and preferably worn at least several hours and more preferably worn overnight. Although the exact mechanism is not well understood, I believe that the material increases the hydration level of the skin over which it is applied, and the increased hydration causes a slight increase in the volume of the local superficial tissue, which serves to tighten the overlying skin and reduce the size and quantity of fine wrinkles. Over the course of a day the skin returns to its pre-treatment hydration level and the appearance of fine wrinkles may return. It is believed that persistent use gives a more persistent effect.

Unlike Botox, Frownies and surgery, this invention does not act on the underlying musculature or subdermal tissue. And unlike chemical peels and laser resurfacing, this invention is noninvasive.

The silicone-containing material preferably comprises silicone elastomers, silicone gels, or silicone interpenetrating polymer networks.

Interpenetrating polymer networks are defined as a blend of two or more polymers where each material forms a continuous network, each network interpenetrating the other (Sperling. 1981). An IPN is therefore a type of polymer/polymer composite. A true IPN comprises polymeric ingredients which are independently crosslinked. Systems wherein only one component is crosslinked are called semi-IPNs or pseudo-IPN's, such as an IPN of a linear thermoplastic polymer and a thermoset elastomer. However, as used herein, the terms IPN, semi-IPN, and pseudo-IPN are used interchangeably.

A non-exhaustive list of examples of silicone-containing material includes polysiloxane, polydimethylsiloxane, semi-interpenetrating polymer networks of polydimethylsiloxane and polytetrafluoroethylene, and interpenetrating polymer networks of polysiloxane and polytetrafluoroethylene.

Additives having various active ingredients, such as peptides, vitamin compounds, antioxidants, growth factors, glycolic or alpahydroxy acids, etc., may be incorporated into the present invention thereby providing an enhanced effect or other perceived advantages in this market. The hydration effect of the invention is independent of whether such active ingredients are present and actually serves to promote the penetration of such agents if used concomitantly. Preferably, if the silicone-containing material includes an additive or additives, the additive is mixed with the silicone-containing material prior to curing the silicone-containing material.

The product of this invention preferably has several features to provide the desired effect of reducing the appearance of facial wrinkles as well as to promote user acceptance. In particular, the product preferably is self-adhesive (e.g., self-adhering) so that tape or bandages are not required to maintain positioning and skin-contact. The product preferably also is not so thick as to be cumbersome, but at the same time preferably is not so thin as to roll-up or wrinkle with normal use. Further, the product preferably has a good "hand quality" and the outer surface preferably is slick as to minimize friction and adherence to bed linen. The product preferably is cut into convenient shapes for application to the proper anatomical regions of the face or body.

In one preferred embodiment of the invention, the invention has each of the above-mentioned features. In this preferred embodiment, the invention comprises a self-adhesive flexible skin patch which acts to noninvasively reduce facial wrinkles without action on the underlying musculature or subdermal tissue. The skin patch in this preferred embodiment has (1) an adhesive skin contacting layer that adheres to skin by itself without the need of tape or the like to secure it in place and (2) a non-adhesive outer layer. The adhesive skin-contacting layer is a silicone-containing material (e.g., a compound containing silicone), and the non-adhesive outer layer is fabric. The skin patch may contain an active ingredient, preferably mixed with the silicone-containing material prior to curing the silicone-containing material, to provide an enhanced effect or other perceived advantage in the market. Examples of the active ingredient include one or more of the following: a peptide, a vitamin compound, an antioxidant, a growth factor, a glycolic or alphahydroxy acid, or combinations thereof.

Exemplary of this embodiment is a patch made using Oleeva® Fabric material. I have found that in this preferred embodiment of the invention Oleeva® Fabric material, commercially marketed by Bio Med Sciences for scar management, has the above-mentioned features and provides a near-ideal wrinkle reduction patch. Oleeva® Fabric material comprises two layers, one of silicone gel in an interpenetrating polymer network with polytetrafluoroethylene and the other of a tricot fabric.

During testing of the invention, pieces of cut Oleeva® Fabric material were applied to one side of a patient's face in the periorbital region for approximately 8 hours overnight. After one treatment the appearance of fine wrinkles at the treatment area was reduced relative to the untreated side. The patient rated the effect as "significant."

Further study showed that the wrinkle reduction effect provided by my invention was noticeable after as little as 2 hours of use, thereby strongly indicating hydration as the primary mechanism of action and ruling out action on underlying musculature and subdermal tissue.

In use, the inventive patch is positioned in place by applying the skin contacting surface of the skin patch over and into contact with the facial wrinkles, and the skin patch is maintained in place over and in contact with the facial wrinkles for an effective amount of time to tighten the skin at and around the facial wrinkles, thereby reducing the reappearance of the facial wrinkles in said skin. Contacting the skin at and near the facial wrinkles with the skin contacting surface of the skin patch results in hydrating the skin at the facial wrinkles to cause an increase of volume in local superficial tissue covered by said skin, thereby tightening the skin overlying the local superficial tissue and reducing the facial wrinkles formed in said skin.

The skin patch also may be used for non-invasively reducing an infra-orbital shadow, striae, lentigo senilis, or hyper/hypo pigmentation formed at a treatment area on a person's skin. In use, the skin patch is positioned by applying the skin contacting surface of the skin patch over and into contact with the infra-orbital shadow, striae, lentigo senilis, or hyper/hypo pigmentation formed at the treatment area, and the skin patch is maintained in place over and in contact with the infra-orbital shadow, striae, lentigo senilis, or hyper/hypo pigmentation formed at the treatment area for an effective amount of time to tighten the skin in the treatment area, thereby reducing the infra-orbital shadow, striae, lentigo senilis, or hyper/hypo pigmentation in the skin. Contacting the skin at the infra-orbital shadow, striae, lentigo senile, or hyper/hypo pigmentation at the treatment area with the skin contacting surface of the skin patch hydrates the skin in the treatment area to cause an increase volume in local superficial tissue covered by said skin, thereby tightening the skin overlying the local superficial tissue and reducing the facial infra-orbital shadow, striae, lentigo senile, or hyper/hypo pigmentation in the skin.

DETAILED DESCRIPTION OF PREFERRED EMBODIMENTS

The following examples are not intended to be limiting. Likewise, it is believed that some materials may be substituted for those disclosed in the examples and still achieve a substantially similar result. Additionally, there are numerous active ingredients that may be useful for wrinkle reduction and treatment of other indications, such as striae ("stretch marks"), lentigo senilis ("age spots") or hyper/hypo pigmentation.

Example 1

Figure 1:
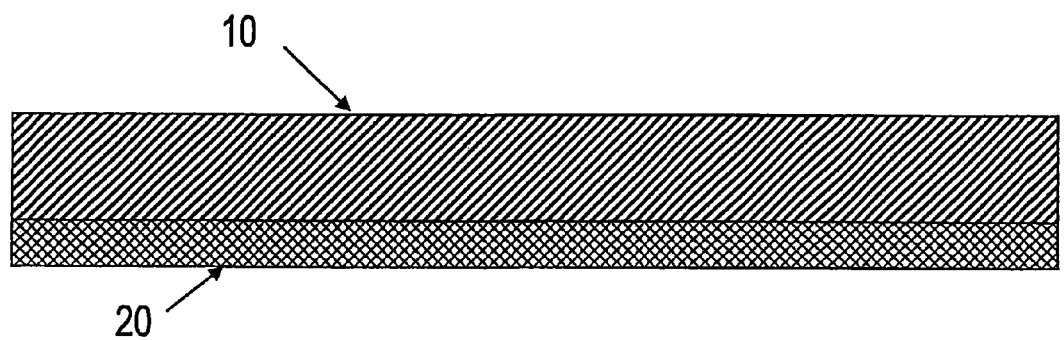
FIG. 1 shows a cross-sectional view of a preferred embodiment of this invention. An IPN material 10 is bonded to a fabric layer 20.
Figure 2:
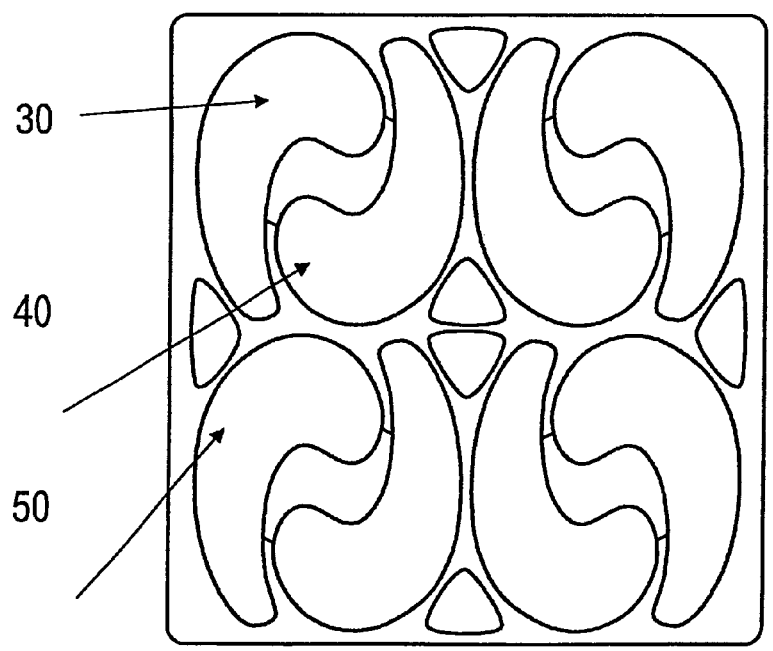
FIG. 2 shows a top plan view of a cutting pattern intended to provide shapes to cover specific facial areas as well as minimize waste in the cutting process of the invention. Piece 30 is designed for the infra-orbital area and commissure of the eye lids, piece 40 may be used between the eye brows, and piece 50 may be used at the corners of the mouth.

A continuous roll of Oleeva® Fabric material was manufactured according to established methods as described in my previously patents cited above. Pieces of the material were cut into the pattern shown in FIG. 2 using a computer controlled laser engraving apparatus to form patches having various shapes to facilitate use at the infra-orbital area and commissure of the eye lids, between the eye brows, and at the corners of the mouth. Patches made from Oleeva® Fabric material having other shapes were made to facilitate use over striae ("stretch marks"), lentigo senilis ("age spots"), and hyper/hypo pigmentation.

The patches were applied over facial wrinkles, infra-orbital shadows, striae ("stretch marks"), lentigo senilis ("age spots"), and hyper/hypo pigmentation for various lengths of time, ranging from about two hours to about eight hours. No tape or the like was needed to secure the patches in place since the skin contacting surface of the patches is self-adhering to skin. The reduction of the appearance of facial wrinkles, infra-orbital shadows ("dark circles"), striae ("stretch marks"), lentigo senilis ("age spots"), and hyper/hypo pigmentation was noticeable after as little as two hours of use and was significant after approximately eight hours of use.

Example 2

The manufacturing process of Example 1 was repeated with the addition of 2 percent by weight of a peptide formulation (available under the trademark "Haloxyl" from The Personal Forulator, Evanstown, Wyo., and promoted as being effective for reducing infra-orbital shadows or "dark circles" under the eyes) containing Glycerin, Steareth-20, hydroxysuccinimide, Chrysin, Palmitoyl Oligopeptide, and Palmitoyl Tetrapeptide-7, being mixed into the silicone-containing layer prior to the silicone-containing layer being cured. For example, the Oleeva Fabric material having the additive peptide formulation in this example of the invention may be manufactured by (1) mixing the additive into liquid PDMS to form a PDMS/additive mixture, (2) casting the liquid PDMS/additive mixture onto a microporous or expanded PTFE membrane or alternatively casting a layer of the liquid PDMS/additive mixture onto a carrier substrate and laying down a microporous or expanded PTFE membrane onto the liquid PDMS/additive mixture layer, whereby natural wicking occurs by way of capillary action to effect impregnation of a portion of the liquid PDMS/additive mixture layer into the PTFE membrane, (3) causing the liquid PDMS/additive mixture to crosslink into a solid elastomer or gel by using heat or some other method of vulcanization, thereby creating an IPN sheet having essentially a PDMS/additive skin-contacting surface and a distal or upper surface comprised of the IPN polymer blend structure, and (4) bonding a fabric layer to the distal or upper surface via use of an adhesive or a layer of liquid PDMS with heat. Alternatively, for example, the manufacturing process also may comprise (1) mixing the additive into liquid PDMS to form a PDMS/additive mixture, (2) casting a layer of the liquid PDMS/additive mixture onto a carrier substrate and laying down a microporous or expanded PTFE membrane onto the liquid PDMS/additive mixture layer and allowing or causing a portion of the liquid PDMS/additive mixture layer to impregnate the PTFE membrane, (3) applying a backing material (e.g., fabric) to the distal surface of the impregnated membrane, and (4) feeding the layered structure formed by the above three steps through an oven for a curing step, with pressure placed on the surface of the layered structure, resulting in solidifying the liquid PDMS/additive mixture in the layered structure and causing a bond to form between the backing material and the impregnated membrane. If desired, the backing material may be laminated to the PTFE membrane using an adhesive prior to laying down the PTFE membrane onto the liquid mixture layer.

Patches formed by pieces 30 were applied over infra-orbital shadows for various lengths of time, ranging from about two hours to about eight hours. No tape or the like was needed to secure the patches in place since the skin contacting surface of the patches is self-adhering to skin. The reduction of the appearance of the infra-orbital shadows was noticeable after as little as two hours of use and was significant after about eight hours of use.

Example 3

The manufacturing process of Example 2 was repeated, expect that the addition of the 2 percent by weight of the peptide formulation detailed in Example 2 was replaced with the addition of 10 percent by weight of a peptide formulation containing hydroglycolic extract of polymannuronate extracted from *Macrocystis pyrifera* being mixed into the silicone-containing layer prior to the silicone-containing layer being cured. The peptide formulation of this example is promoted as being effective for improving skin firmness and decreasing facial wrinkles.

The patches were applied over facial wrinkles for various lengths of time, ranging from about two hours to about eight hours. No tape or the like was needed to secure the patches in place since the skin contacting surface of the patches is self-adhering to skin. The reduction of the appearance of facial wrinkles was noticeable after as little as two hours use and was significant after about eight hours of use.

The invention claimed is:

1. A method of noninvasively reducing facial wrinkles formed in facial skin, comprising the steps of
   providing a skin patch comprising a membrane and having a skin contacting surface, the skin contacting surface comprising a film of silicone-containing material to which an additive has been added to said silicone-containing material prior to cross-linking of the silicone-containing material, said silicone-containing material having the additive impregnated therein and after cross-linking of the silicone-containing material to said membrane,
   wherein said additive is a therapeutic active ingredient,
   wherein said skin patch skin contacting surface comprises a cross-linked composition of said silicone-containing material and said therapeutic active ingredient on said membrane, said silicone-containing material being cross-linked to said membrane,
   applying the skin contacting surface of the skin patch over and into contact with facial wrinkles, and
   maintaining the skin patch in place over and in contact with the facial wrinkles for an effective amount of time to tighten the skin at and around the facial wrinkles, thereby reducing the facial wrinkles in said skin, by contacting the skin with said skin patch silicone material film and delivering a treatment of said active ingredient contained in said patch to said skin by contacting the skin with the already cross-linked together surface of silicone-containing material and membrane containing said active ingredient to deliver said active ingredient from said film;
   the additive being useful for wrinkle reduction and/or other clinical indications; and
   the additive being peptides, vitamin compounds, antioxidants, growth factors, glycolic or alphahydroxy acids, or combinations thereof.

2. The method of claim 1, further including
   hydrating the skin at the facial wrinkles by contacting the skin at and near the facial wrinkles with the skin contacting surface of the skin patch to cause an increase in volume in local superficial tissue covered by said skin, thereby tightening the skin overlying the local superficial tissue and reducing the facial wrinkles formed in said skin.

3. The method of claim 1, further including
affixing the skin patch in place over the wrinkles by pressing the skin patch against the facial wrinkles, the skin patch being self-adhering to facial skin.

4. The method of claim 1,
the silicone-containing material being a silicone elastomer, a silicone gel, or a silicone interpenetrating polymer network.

5. The method of claim 1,
the silicone-containing material being polysiloxane.

6. The method of claim 1,
the silicone-containing material being polydimethylsiloxane.

7. The method of claim 1,
the silicone-containing material being an interpenetrating polymer network of polysiloxane and polytetrafluoroethylene, and wherein said additive is mixed with said polysiloxane to form a polysiloxane/additive mixture, and wherein the polysiloxane/additive mixture is applied onto the polytetrafluoroethylene to impregnate said polytetrafluoroethylene with said polysiloxane/additive mixture, said polytetrafluoroethylene being impregnated with said polysiloxane/additive mixture, and, after cross-linking of the silicone-containing material, said membrane comprising a cross-linked solid or elastomer gel that is an interpenetrating polymer network having a polysiloxane/additive skin-contacting surface and a distal or upper surface comprised of the interpenetrating polymer network of polysiloxane and polytetrafluoroethylene.

8. The method of claim 1,
the silicone-containing material being a semi-interpenetrating polymer network of polydimethylsiloxane and polytetrafluoroethylene, and wherein said additive is mixed with said polydimethylsiloxane to form a polydimethylsiloxane/additive mixture, and wherein the polydimethylsiloxane/additive mixture is applied onto the polytetrafluoroethylene to impregnate said polytetrafluoroethylene with said polydimethylsiloxane/additive mixture, said polytetrafluoroethylene being impregnated with said polydimethylsiloxane/additive mixture, and, after cross-linking of the silicone-containing material, said membrane comprising a cross-linked solid or elastomer gel that is a semi-interpenetrating polymer network having a polydimethylsiloxane/additive skin-contacting surface and a distal or upper surface comprised of the semi-interpenetrating polymer network of polysiloxane and polytetrafluoroethylene.

9. The method of claim 8, the skin patch having an outer layer opposite the skin contacting surface, the outer layer having a slick outer surface to minimize friction and adherence to bed linen, the outer layer being a fabric, and the silicone-containing material that is provided being formed by a step of bonding the fabric layer to the distal or upper surface.

10. The method of claim 1,
the skin patch having an outer layer opposite the skin contacting surface, the outer layer having a slick outer surface to minimize friction and adherence to bed linen.

11. The method of claim 10,
the outer layer being a fabric.

12. The method of claim 1, wherein said membrane is PTFE.

13. A method of noninvasively reducing an infra-orbital shadow, striae; lentigo senilis, or hyper/hypo pigmentation formed at a treatment area on a person's skin, comprising the steps of
providing a skin patch comprising a membrane and having a skin contacting surface, the skin contacting surface comprising a film of silicone-containing material to which an additive has been added to said silicone-containing material prior to cross-linking of the silicone-containing material, said silicone-containing material having the additive impregnated therein and after cross-linking of the silicone-containing material to said membrane,
applying the skin contacting surface of the skin patch over and into contact with the infra-orbital shadow, striae, lentigo senilis, or hyper/hypo pigmentation formed at the treatment area, and
maintaining the skin patch in place over and in contact with the infra-orbital shadow, striae, lentigo senilis, or hyper/hypo pigmentation formed at the treatment area for an effective amount of time to tighten the skin in the treatment area, thereby reducing the infra-orbital shadow, striae, lentigo senilis, or hyper/hypo pigmentation in said skin;
wherein said skin patch skin contacting surface comprises a cross-linked composition of said silicone-containing material and said additive on said membrane, said silicone-containing material being cross-linked to said membrane, and
wherein said additive comprises an active ingredient, and wherein applying the skin patch includes delivering the active ingredient from the patch into which it is impregnated to the skin;
the additive being useful for wrinkle reduction and/or other clinical indications; and
the additive being peptides, vitamin compounds, antioxidants, growth factors, glycolic or alphahydroxy acids, or combinations thereof.

14. The method of claim 13, further including
hydrating the skin in the treatment area by contacting said skin at and near the infra-orbital shadow, striae, lentigo senilis, or hyper/hypo pigmentation at the treatment area with the skin contacting surface of the skin patch to cause an increase in volume in local superficial tissue covered by said skin, thereby tightening the skin overlying the local superficial tissue and reducing the infra-orbital shadow, striae, lentigo senilis, or hyper/hypo pigmentation in said skin.

15. The method of claim 13, further including
affixing the skin patch in place over the treatment area by pressing the skin patch against the treatment area, the skin patch being self-adhering to the treatment area.

16. The method of claim 13,
the silicone-containing material being a silicone elastomer, a silicone gel, or a silicone elastomer, a silicone gel, or a silicone interpenetrating polymer network.

17. The method of claim 13,
the silicone-containing material being polysiloxane.

18. The method of claim 13,
the silicone-containing material being polydimethylsiloxane.

19. The method of claim 13,
the silicone-containing material being an interpenetrating polymer network of polysiloxane and polytetrafluoroethylene, and wherein said additive is mixed with said polysiloxane to form a polysiloxane/additive mixture, and wherein the polysiloxane/additive mixture is applied onto the polytetrafluoroethylene to impregnate said polytetrafluoroethylene with said polysiloxane/additive mixture, said polytetrafluoroethylene being impregnated with said polysiloxane/additive mixture, and, after cross-linking of the silicone-containing material, said membrane comprising a cross-linked solid or elastomer gel that is an interpenetrating polymer network having a polysiloxane/additive skin-contacting surface and a distal or upper surface comprised of the interpenetrating polymer network of polysiloxane and polytetrafluoroethylene.

20. The method of claim 13,
the silicone-containing material being a semi-interpenetrating polymer network of polydimethylsiloxane and polytetrafluoroethylene, and wherein said additive is mixed with said polydimethylsiloxane to form a polydimethylsiloxane/additive mixture, and wherein the polydimethylsiloxane/additive mixture is applied onto the polytetrafluoroethylene to impregnate said polytetrafluoroethylene with said polydimethylsiloxane/additive mixture, said polytetrafluoroethylene being impregnated with said polydimethylsiloxane/additive mixture, and, after cross-linking of the silicone-containing material, said membrane comprising a cross-linked solid or elastomer gel that is a semi-interpenetrating polymer network having a polydimethylsiloxane/additive skin-contacting surface and a distal or upper surface comprised of the semi-interpenetrating polymer network of polysiloxane and polytetrafluoroethylene.

21. The method of claim 13,
the skin patch having an outer layer opposite the skin contacting surface, the outer layer having a slick outer surface to minimize friction and adherence to bed linen.

22. The method of claim 21,
the outer layer being a fabric.

23. A method of noninvasively reducing facial wrinkles formed in facial skin, comprising the steps of
providing a skin patch comprising a membrane and having a skin contacting surface, the skin contacting surface comprising a film of silicone-containing material to which an additive has been added to said silicone-containing material prior to cross-linking of the silicone-containing material, said silicone-containing material having the additive impregnated therein and after cross-linking of the silicone-containing material to said membrane,
wherein said additive is a therapeutic active ingredient,
wherein said skin patch skin contacting surface comprises a cross-linked composition of said silicone-containing material and said therapeutic active ingredient on said membrane, said silicone-containing material being cross-linked to said membrane,
applying the skin contacting surface of the skin patch over and into contact with facial wrinkles, and
maintaining the skin patch in place over and in contact with the facial wrinkles for an effective amount of time to tighten the skin at and around the facial wrinkles, thereby reducing the facial wrinkles in said skin, by contacting the skin with said skin patch silicone material film and delivering a treatment of said active ingredient contained in said patch to said skin by contacting the skin with the already cross-linked together surface of silicone-containing material and membrane containing said active ingredient to deliver said active ingredient from said film;
wherein said additive comprises an active ingredient selected from the group consisting of: a peptide, a vitamin compound, an antioxidant, a growth factor, a glycolic, alphahydroxy acid, and combinations thereof, and wherein treating comprises treating said skin with said active ingredient contained in said film of silicone-containing material in which said active ingredient has been added prior to cross-linking of the silicone-containing material with said membrane.

24. A method of noninvasively reducing facial wrinkles formed in facial skin, comprising the steps of
providing a skin patch comprising a membrane and having a skin contacting surface, the skin contacting surface comprising a film of silicone-containing material to which an additive has been added to said silicone-containing material prior to cross-linking of the silicone-containing material, said silicone-containing material having the additive impregnated therein and after cross-linking of the silicone-containing material to said membrane,
wherein said additive is a therapeutic active ingredient,
wherein said skin patch skin contacting surface comprises a cross-linked composition of said silicone-containing material and said therapeutic active ingredient on said membrane, said silicone-containing material being cross-linked to said membrane,
applying the skin contacting surface of the skin patch over and into contact with facial wrinkles, and
maintaining the skin patch in place over and in contact with the facial wrinkles for an effective amount of time to tighten the skin at and around the facial wrinkles, thereby reducing the facial wrinkles in said skin, by contacting the skin with said skin patch silicone material film and delivering a treatment of said active ingredient contained in said patch to said skin by contacting the skin with the already cross-linked together surface of silicone-containing material and membrane containing said active ingredient to deliver said active ingredient from said film;
wherein said additive comprises a peptide formulation containing Glycerin, Steareth-20, hydroxysuccinimide, Chrysin, Palmitoyl Oligopeptide, and Palmitoyl Tetrapeptide-7.

25. A method of noninvasively reducing facial wrinkles formed in facial skin, comprising the steps of
providing a skin patch comprising a membrane and having a skin contacting surface, the skin contacting surface comprising a film of silicone-containing material to which an additive has been added to said silicone-containing material prior to cross-linking of the silicone-containing material, said silicone-containing material having the additive impregnated therein and after cross-linking of the silicone-containing material to said membrane,
wherein said additive is a therapeutic active ingredient,
wherein said skin patch skin contacting surface comprises a cross-linked composition of said silicone-containing material and said therapeutic active ingredient on said membrane, said silicone-containing material being cross-linked to said membrane,
applying the skin contacting surface of the skin patch over and into contact with facial wrinkles, and
maintaining the skin patch in place over and in contact with the facial wrinkles for an effective amount of time to tighten the skin at and around the facial wrinkles, thereby reducing the facial wrinkles in said skin, by contacting the skin with said skin patch silicone material film and delivering a treatment of said active ingredient contained in said patch to said skin by contacting the skin with the already cross-linked together surface of silicone-containing material and membrane containing said active ingredient to deliver said active ingredient from said film;
wherein said additive comprises a peptide formulation containing hydroglycolic extract of polymannuronate extracted from *Macrocystis pyrifera*.

* * * * *